US00PP33352P2

(12) United States Plant Patent
Olesen

(10) Patent No.: US PP33,352 P2
(45) Date of Patent: Aug. 17, 2021

(54) FLORIBUNDA ROSE PLANT NAMED 'POULPAL084'

(50) Latin Name: *Rosa hybrida*
Varietal Denomination: Poulpal084

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,983

(22) Filed: Sep. 3, 2020

(51) Int. Cl.
*A01H 5/02* (2018.01)
*A01H 6/74* (2018.01)

(52) U.S. Cl.
USPC ..... Plt./143

(58) Field of Classification Search
USPC ..... Plt./101, 141, 143
See application file for complete search history.

*Primary Examiner* — Susan McCormick Ewoldt

(57) ABSTRACT

A new garden rose plant of the Compact Floribunda class which has abundant, apricot pink blend flowers and attractive foliage. This new and distinct variety has shown to be uniform and stable in the resulting generations from asexual propagation.

1 Drawing Sheet

Botanical designation: *Rosa hybrida.*
Variety denomination: 'Poulpal084'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpal084', originated as a single seedling from the stated cross.

The new variety may be distinguished from its male pollen parent and female seed parent primarily by the following characteristics. The male pollen parent plant has near white flowers while the new variety has apricot pink blend flowers. The female seed parent plant has orange red flowers while the new variety has apricot pink blend flowers.

The objective of the hybridization of this rose variety was to create a new and distinct variety with unique qualities, such as:

1. Uniform and abundant apricot pink blend flowers;
2. Vigorous, but compact growth when propagated on its own roots;
3. Exceptional disease resistance.

This combination of qualities is not present in previously available commercial cultivars of this type, known to the inventor, and distinguish 'Poulpal084' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpal084' was selected in the spring of 2012 by the inventor as a single plant from the progeny of the aforementioned hybridization.

Asexual reproduction of 'Poulpal084' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpal084' are true to type and are transmitted from one generation to the next.

DESCRIPTION OF THE DRAWING

The accompanying color illustration shows, as true as is reasonably possible in images of this type, the typical characteristics of 'Poulpal084'.

Specifically illustrated in this drawing are an open flower, flower buds at various stages of development, receptacle, pedicel, bare stems, and leaves. Plants shown are 2 years of age.

DETAILED DESCRIPTION OF THE VARIETY

The following is a description of 'Poulpal084', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpal036', U.S. Plant Pat. No. 24,635 are compared to 'Poulpal084' in Chart 1.

CHART 1

| | 'Poulpal084' | 'Poulpal036' |
|---|---|---|
| Petal Count | 35 | 65 |
| Flower Diameter | 85 mm | 85 mm |
| General Tonality | Orange Group 25D | Red-Purple Group |

CHART 1-continued

| | 'Poulpal084' | 'Poulpal036' |
|---|---|---|
| of Flower Color | and Red-Purple Group 62A | 58C |

FLOWER AND FLOWER BUD

Blooming habit: Continuous.

Flower bud:

*Size*.—Upon opening, 26 mm in length from base of receptacle to end of bud. Bud diameter is 15 mm.

*Bud form*.—Ovoid.

*Bud color*.—As sepals divide petals are Greyed-Red Group 180B and Red Group N34A.

*Sepal inner surface*.—Color: Yellow-Green Group 146D. Surface: Lightly pubescent.

*Sepal outer surface*.—Color: Yellow-Green Group 144A intoned Greyed-Red Group 181A. Texture: Slightly rough with numerous fragrant stipitate glands.

*Sepal shape*.—Apex: Cirrhose. Base: Flat at union with receptacle.

*Sepal margin*.—Margins have moderate foliaceous appendages on three of the five sepals.

*Sepal size*.—About 21 mm long, 8 mm wide.

*Receptacle*.—Texture: Smooth. Size: 6 mm in height, 10 mm wide. Color: Yellow-Green Group 144A with light intonations of Greyed-Red Group 179B. Shape: Campanulate and funnel shape combinations.

*Pedicel*.—Surface: Smooth. Length: 25 mm. Diameter: 2 mm on average. Color: Yellow-Green Group 144A with intonations of Greyed-Orange Group 171A. Strength: Strong.

*Peduncle*.—Length: 1 cm. Diameter: About 3 mm. Color: Yellow-Green Group 144A. Texture: Smooth.

Flower bud development: Flower buds are borne singly or in clusters of 3 flower buds per stem.

Flower bloom:

*Fragrance*.—Moderate.

*Duration*.—The blooms have a duration on the plant of approximately 14 days. Petals fall cleanly away from plant after flowers have fully matured.

*Size*.—Flower diameter is 85 mm when open. Flower depth is 35 mm.

*Flower shape*.—Open cup, double flower, with petals that curve out from the center. The upper portion is convex, and the lower portion is flat concave.

Petalage: Under normal conditions, flowers have about 35 petals.

General tonality of flower: Open flowers are Orange Group 25D and Red-Purple Group 62A.

Petal color:

*Upon opening, outer petals*.—Upper surface: Orange Group 24C splashed with Yellow Group 4D at the basal zone, splashed with Red-Purple Group 62C at the middle zone, and Red-Purple Group 63B at the marginal zone. Lower surface: Red Group 49D with 49A.

*Upon opening, inner petals*.—Upper surface: At the basal zone, Yellow Group 4D, at the middle zone Orange Group 24C blended with Red-Purple Group 62C. Lower surface: Red Group 49D with 49A.

*Basal petal spots, upon opening*.—No distinctive coloration at the petal base observed.

Petals:

*Petal reflex*.—Somewhat reflexed.

*Margin*.—Entire and uniform. Strong undulations.

*Shape*.—Broad and elliptic. Apex shape: Rounded. Base shape: Acute.

*Size*.—45 mm (l)×40 mm (w).

*Texture*.—Smooth.

*Thickness*.—Average.

Petaloids: None observed.

Reproductive flower parts:

*Pollen*.—None observed.

*Anthers*.—Size: 2 mm in length. Color: Greyed-Yellow Group 160A. Quantity: 36 on average.

*Filaments*.—Color: Yellow Group 12C. Length: 6 mm.

*Pistils*.—Length: 7 mm. Quantity: 29 on average.

*Stigmas*.—Color: Green-White Group 157A.

*Styles*.—Color: Green-White Group 157A.

*Location of stigmas*.—Inferior in location relative to the length of the filaments and the height of the anthers.

*Hips*.—None Observed.

PLANT

Plant growth: Upright, compact and well branched. Plants are 35 cm in height, and 35 cm wide.

Stems:

*Color of juvenile growth*.—Yellow-Green Group 144B.

*Color of mature growth*.—Yellow-Green Group 144A.

*Length*.—Canes are about 15 cm from the base of the plant to the flowering portion.

*Diameter*.—About 6 mm.

*Internodes*.—On mature canes about 37 mm between nodes.

*Surface texture*.—Young wood: Rough with small prickles. Older wood: Rough with small prickles.

Long prickles:

*Incidence*.—13 prickles per 10 cm of stem.

*Size*.—Average length of prickles on mature stems is 4 mm.

*Shape*.—Upper portion is linear. Lower portion is concave.

*Color*.—Juvenile prickles: Greyed-Red Group 180A. Mature prickles: Greyed-Red Group 180A.

Plant foliage:

*Compound leaf*.—98 mm (l)×84 (w).

*Quantity*.—2 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 15 mm long, mm wide. Quantity: 2 per compound leaf. Shape: Linear, slightly broad based with outward extending apices. Margins: Finely serrated. Color:

*Petiole*.—Length: 20 mm. Diameter: 2 mm. Upper surface color: Yellow-Green Group 144A. Lower surface color: Yellow-Green Group 144A.

*Rachis*.—Length: 28 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 48 mm long, 30 mm wide. Shape: Generally elliptical. Base: Rounded. Apex: Acute. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal084', substantially as illustrated and described herein, due to its abundant apricot pink blend flowers, disease resistance, and extended period of bloom.

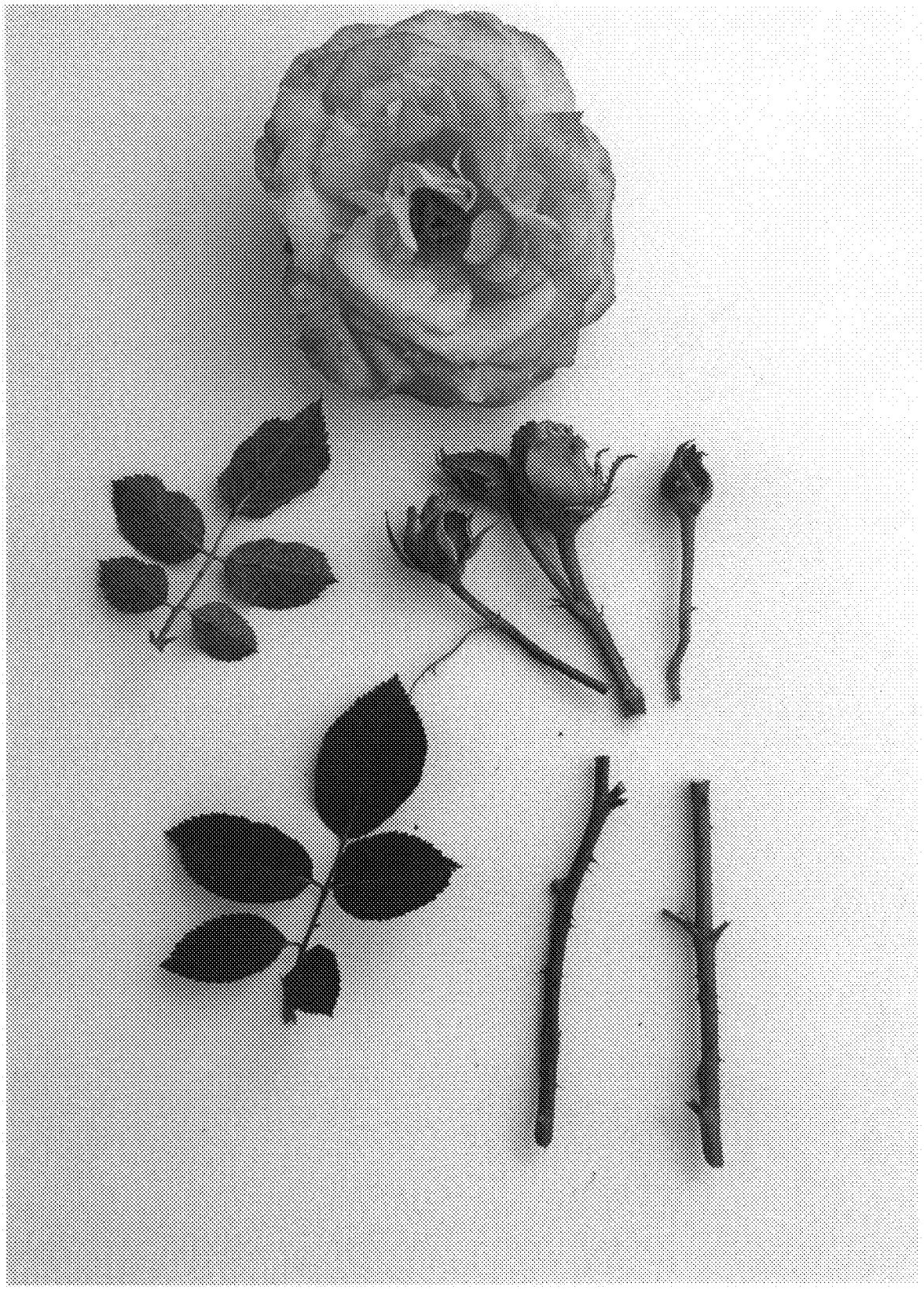

* * * * *